(12) United States Patent
Dyer et al.

(10) Patent No.: US 8,827,870 B2
(45) Date of Patent: Sep. 9, 2014

(54) EXERCISE GUIDANCE SYSTEM

(75) Inventors: David E. Dyer, Renton, WA (US);
James S. Birrell, Seattle, WA (US);
Brady A. Olason, Mukilteo, WA (US);
Brian D. Wilson, Bothell, WA (US);
David W. Flynt, Lake Forest Park, WA (US); Autumn L. Stroupe, Kirkland, WA (US)

(73) Assignee: Precor Incorporated, Woodinville, WA (US)

( * ) Notice: Subject to any disclaimer, the term of this patent is extended or adjusted under 35 U.S.C. 154(b) by 834 days.

(21) Appl. No.: 12/572,448

(22) Filed: Oct. 2, 2009

(65) Prior Publication Data

US 2011/0082010 A1    Apr. 7, 2011

(51) Int. Cl.
*A63B 71/00*    (2006.01)
*G06F 19/00*    (2011.01)
*A63B 71/06*    (2006.01)
*A63B 24/00*    (2006.01)

(52) U.S. Cl.
CPC ......... *A63B 24/0062* (2013.01); *A63B 71/0622* (2013.01); *G06F 19/3481* (2013.01); *A63B 2024/0065* (2013.01); *A63B 2225/20* (2013.01); *A63B 24/0075* (2013.01)
USPC .......................................................... 482/9

(58) Field of Classification Search
USPC .................. 482/1–9, 148, 900–902; 434/247
See application file for complete search history.

(56) References Cited

U.S. PATENT DOCUMENTS

| | | | |
|---|---|---|---|
| 4,720,789 A | 1/1988 | Hector et al. | 463/33 |
| 4,828,257 A | 5/1989 | Dyer et al. | 482/5 |
| 4,840,372 A | 6/1989 | Oglesby et al. | 482/9 |
| 4,907,795 A * | 3/1990 | Shaw et al. | 482/9 |
| 4,955,602 A | 9/1990 | Rastelli | 482/84 |
| 4,998,725 A | 3/1991 | Watterson et al. | 482/6 |
| 5,062,626 A | 11/1991 | Dalebout et al. | 482/1 |
| 5,062,632 A | 11/1991 | Dalebout et al. | 482/7 |
| 5,067,710 A | 11/1991 | Watterson et al. | 482/3 |
| 5,104,120 A | 4/1992 | Watterson et al. | 482/5 |
| 5,149,084 A | 9/1992 | Dalebout et al. | 482/3 |
| 5,213,555 A | 5/1993 | Hood et al. | 482/57 |
| 5,383,826 A | 1/1995 | Michael | 482/3 |
| 5,466,200 A | 11/1995 | Ulrich et al. | 482/4 |
| 5,484,355 A | 1/1996 | King, II et al. | 482/4 |
| 5,489,249 A | 2/1996 | Brewer et al. | 482/5 |
| 5,512,025 A | 4/1996 | Dalebout et al. | 482/6 |
| 5,554,033 A | 9/1996 | Bizzi et al. | 434/247 |
| 5,591,104 A | 1/1997 | Andrus et al. | 482/7 |
| 5,645,509 A | 7/1997 | Brewer et al. | 482/4 |
| 5,655,997 A | 8/1997 | Greenberg et al. | 482/5 |
| 5,706,822 A | 1/1998 | Khavari | 600/483 |
| 5,777,895 A | 7/1998 | Kuroda et al. | 702/188 |
| 5,785,632 A | 7/1998 | Greenberg et al. | 482/5 |
| 5,888,172 A | 3/1999 | Andrus et al. | 482/7 |
| 5,890,995 A | 4/1999 | Bobick et al. | 482/4 |
| 5,916,063 A | 6/1999 | Alessandri | 482/4 |
| 5,931,763 A | 8/1999 | Alessandri | 482/4 |
| 6,042,519 A | 3/2000 | Shea | 482/57 |
| 6,053,844 A | 4/2000 | Clem | 482/8 |
| 6,059,692 A | 5/2000 | Hickman | 482/8 |
| 6,066,075 A | 5/2000 | Poulton | 482/8 |

(Continued)

*Primary Examiner* — Robert Long
(74) *Attorney, Agent, or Firm* — Terence P. O'Brien; Todd A. Rathe (57) ABSTRACT

An exercise guidance system and method dynamically adjusts an exercise route for meeting a fitness objective based upon a comparison of the route and actual received exercise metrics on an exercise device.

20 Claims, 4 Drawing Sheets

(56) References Cited

U.S. PATENT DOCUMENTS

| | | | |
|---|---|---|---|
| 6,152,856 A | 11/2000 | Studor et al. | 482/8 |
| 6,159,131 A | 12/2000 | Pfeffer | 482/8 |
| 6,171,218 B1 | 1/2001 | Shea | 482/57 |
| 6,193,631 B1 | 2/2001 | Hickman | 482/8 |
| 6,227,968 B1 | 5/2001 | Suzuki et al. | 463/7 |
| 6,244,988 B1 | 6/2001 | Delman | 482/8 |
| 6,312,363 B1 | 11/2001 | Watterson et al. | 482/54 |
| 6,330,499 B1 | 12/2001 | Chou et al. | 701/33 |
| 6,336,891 B1 | 1/2002 | Fedrigon et al. | 482/8 |
| 6,421,571 B1 | 7/2002 | Spriggs et al. | 700/17 |
| 6,447,424 B1 | 9/2002 | Ashby et al. | 482/8 |
| 6,458,060 B1 | 10/2002 | Watterson et al. | 482/54 |
| 6,464,618 B1 | 10/2002 | Shea | 482/8 |
| 6,475,115 B1 | 11/2002 | Candito et al. | 482/4 |
| 6,511,404 B2 * | 1/2003 | Tu | 482/57 |
| 6,514,199 B1 | 2/2003 | Alessandri | 600/300 |
| 6,554,706 B2 | 4/2003 | Kim et al. | 463/36 |
| 6,572,512 B2 | 6/2003 | Anderson et al. | 482/51 |
| 6,601,016 B1 | 7/2003 | Brown et al. | 702/182 |
| 6,616,578 B2 | 9/2003 | Alessandri | 482/8 |
| 6,626,799 B2 | 9/2003 | Watterson et al. | 482/4 |
| 6,626,800 B1 | 9/2003 | Casler | 482/8 |
| 6,634,992 B1 | 10/2003 | Ogawa | 482/8 |
| 6,638,198 B1 | 10/2003 | Shea | 482/8 |
| 6,659,916 B1 | 12/2003 | Shea | 482/57 |
| 6,702,719 B1 | 3/2004 | Brown et al. | 482/8 |
| 6,746,371 B1 | 6/2004 | Brown et al. | 482/8 |
| 6,793,607 B2 * | 9/2004 | Neil | 482/8 |
| 6,827,669 B2 | 12/2004 | Cohen et al. | 482/8 |
| 6,863,641 B1 | 3/2005 | Brown et al. | 482/8 |
| 6,866,613 B1 | 3/2005 | Brown et al. | 482/8 |
| 6,902,513 B1 | 6/2005 | McClure | 482/8 |
| 6,918,858 B2 | 7/2005 | Watterson et al. | 482/54 |
| 6,921,351 B1 | 7/2005 | Hickman et al. | 482/8 |
| 6,971,973 B2 | 12/2005 | Cohen et al. | 482/8 |
| 6,991,586 B2 | 1/2006 | Lapcevic | 482/8 |
| 6,997,852 B2 | 2/2006 | Watterson et al. | 482/1 |
| 7,022,047 B2 | 4/2006 | Cohen et al. | 482/8 |
| 7,056,265 B1 | 6/2006 | Shea | 482/8 |
| 7,060,006 B1 | 6/2006 | Watterson et al. | 482/54 |
| 7,060,008 B2 | 6/2006 | Watterson et al. | 482/54 |
| 7,070,539 B2 | 7/2006 | Brown et al. | 482/8 |
| 7,121,982 B2 | 10/2006 | Feldman | 482/8 |
| 7,128,693 B2 | 10/2006 | Brown et al. | 482/8 |
| 7,166,062 B1 | 1/2007 | Watterson et al. | 482/8 |
| 7,166,064 B2 | 1/2007 | Watterson et al. | 482/54 |
| 7,217,224 B2 | 5/2007 | Thomas | 482/8 |
| 7,331,226 B2 | 2/2008 | Feldman et al. | 73/379.01 |
| 7,455,622 B2 | 11/2008 | Watterson et al. | 482/8 |
| 7,491,153 B2 | 2/2009 | Li et al. | 482/8 |
| 7,507,183 B2 | 3/2009 | Anderson et al. | 482/1 |
| 7,521,623 B2 | 4/2009 | Bowen | 84/612 |
| 7,537,546 B2 | 5/2009 | Watterson et al. | 482/8 |
| 7,549,947 B2 | 6/2009 | Hickman et al. | 482/8 |
| 7,556,590 B2 | 7/2009 | Watterson et al. | 482/8 |
| 7,575,536 B1 | 8/2009 | Hickman | 482/8 |
| 7,594,873 B2 | 9/2009 | Terao et al. | 482/1 |
| 7,618,346 B2 | 11/2009 | Crawford et al. | 482/8 |
| 7,621,846 B2 | 11/2009 | Ainsworth et al. | 482/8 |
| 2002/0019258 A1 | 2/2002 | Kim et al. | 463/36 |
| 2002/0022551 A1 | 2/2002 | Watterson et al. | 482/8 |
| 2002/0055383 A1 | 5/2002 | Onda et al. | 463/36 |
| 2002/0055419 A1 | 5/2002 | Hinnebusch | 482/8 |
| 2002/0097150 A1 | 7/2002 | Sandelman et al. | 340/506 |
| 2002/0160883 A1 * | 10/2002 | Dugan | 482/8 |
| 2007/0225118 A1 | 9/2007 | Giorno | 482/1 |
| 2007/0260482 A1 | 11/2007 | Nurmela et al. | 705/2 |
| 2007/0265138 A1 | 11/2007 | Ashby | 482/8 |
| 2007/0265139 A1 | 11/2007 | Glick | 482/8 |
| 2008/0051256 A1 | 2/2008 | Ashby et al. | 482/5 |
| 2008/0153670 A1 | 6/2008 | McKirdy et al. | 482/1 |
| 2008/0161654 A1 | 7/2008 | Teller et al. | 600/300 |
| 2008/0182723 A1 | 7/2008 | Aaron et al. | 482/8 |
| 2008/0200312 A1 * | 8/2008 | Tagliabue | 482/9 |
| 2008/0207401 A1 | 8/2008 | Harding et al. | 482/4 |
| 2008/0220941 A1 | 9/2008 | Shaw et al. | 482/9 |
| 2009/0023553 A1 | 1/2009 | Shim | 482/4 |
| 2009/0075781 A1 | 3/2009 | Schwarzberg et al. | 482/8 |
| 2009/0098980 A1 | 4/2009 | Waters | 482/8 |
| 2009/0098981 A1 | 4/2009 | Del Giorno | 482/9 |
| 2009/0111656 A1 | 4/2009 | Sullivan et al. | 482/4 |
| 2009/0118100 A1 | 5/2009 | Oliver et al. | 482/8 |
| 2009/0139389 A1 | 6/2009 | Bowen | 84/636 |
| 2009/0144080 A1 | 6/2009 | Gray et al. | 705/2 |
| 2009/0156364 A1 | 6/2009 | Simeoni | 482/9 |
| 2009/0163321 A1 | 6/2009 | Watterson et al. | 482/4 |
| 2009/0219159 A1 | 9/2009 | Morgenstern | 340/573.1 |
| 2009/0221404 A1 | 9/2009 | Dorogusker et al. | 482/8 |
| 2009/0233770 A1 | 9/2009 | Vincent et al. | 482/8 |
| 2009/0233771 A1 * | 9/2009 | Quatrochi et al. | 482/9 |
| 2009/0239709 A1 | 9/2009 | Wu | 482/8 |
| 2009/0240113 A1 | 9/2009 | Heckerman | 600/300 |
| 2009/0253554 A1 | 10/2009 | McIntosh | 482/4 |
| 2009/0258710 A1 * | 10/2009 | Quatrochi et al. | 463/43 |
| 2009/0258758 A1 | 10/2009 | Hickman et al. | 482/8 |
| 2009/0262088 A1 | 10/2009 | Moll-Carrillo et al. | 345/173 |
| 2009/0270227 A1 | 10/2009 | Ashby et al. | 482/8 |
| 2009/0298650 A1 * | 12/2009 | Kutliroff | 482/8 |

\* cited by examiner

EXERCISE GUIDANCE SYSTEM

CROSS-REFERENCE TO RELATED PATENT APPLICATIONS

The present application is related to co-pending application Ser. No. 12/572,444 filed on the same date herewith by James S. Birrell, Brady A. Olason, David W. Flynt, Autumn L. Stroupe and David E. Dyer and entitled EXERCISE COMMUNITY SYSTEM, the full disclosure of which is hereby incorporated by reference.

BACKGROUND

Individuals often seek to attain fitness goals. However, maintaining disciplined work out regimens is often difficult due to sickness, work interruptions and various other changes in circumstance. In addition, individuals may not necessarily have workouts designed to meet their fitness goals. As a result, the fitness goals of an individual are often difficult to reach.

DETAILED DESCRIPTION OF THE EXAMPLE EMBODIMENTS

Figure 1:
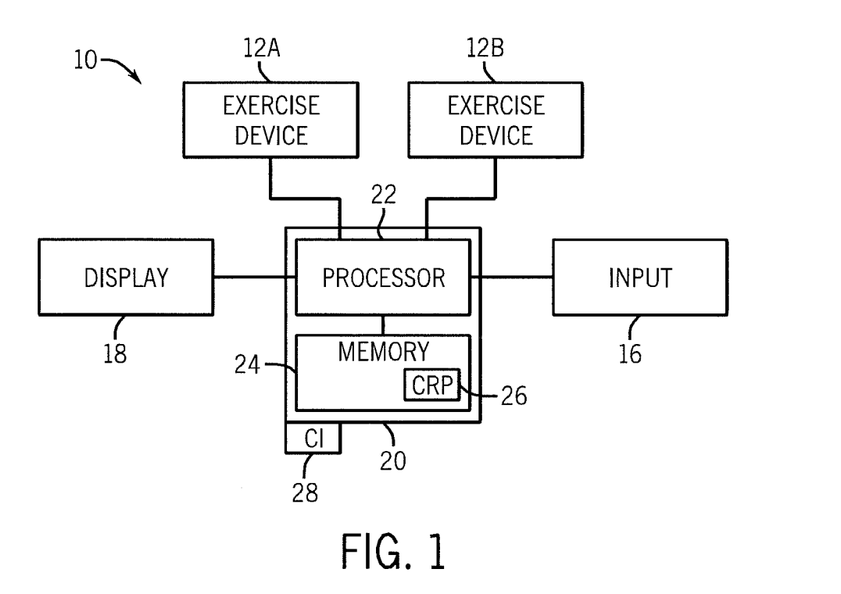
FIG. 1 is a schematic illustration of an exercise guidance system according to an example embodiment.

FIG. 1 schematically illustrates exercise guidance system 10 according to an example embodiment. As will be described hereafter, exercise guidance system 10 identifies an exercise route for achieving one of more fitness objectives or goals using one or more exercise devices and automatically adjusts the route based upon a comparison of exercise results or exercise metrics with the exercise route, user adherence and unplanned or planned user events. As a result; exercise guidance system 10 takes into account interruptions or breaks in an exercise regimen such as sickness, travel, work or life changes interruptions, goal realignment and other changes in circumstances. For purposes of this disclosure, the term "exercise route" shall mean a plan, specification, path, recipe or other step by step directions or instructions for using one or more exercise activities to make progress towards a fitness or other goal objective.

Exercise guidance system 10 includes a plurality of fitness equipment units or exercise devices 12A, 12B (collectively referred to as exercise devices 12), input 16, display 18 and controller 20. Exercise devices 12 comprise exercise machines by which an individual may exercise by applying force or motion to one or movable structures associated with exercise device 12. Exercise devices 12 are configured to sense or measure one or more attributes of an individual such as body weight, body composition and heart rate, as well as a means of collecting subjective user input. Exercise devices 12 are further configured to sense exercise results comprising the power, force or motion applied by the individual exercising such as the rate at which foot supports or swing arms are driven, the rate and incline which a treadmill is driven, the cadence of the user, and the like. The individual attributes sensed by exercise device 12 as well as the exercise results are communicated to controller 20.

In one embodiment, exercise devices 12 communicate with controller 20 in a wired fashion. In another embodiment, exercise devices 12 communicate with controller 20 in a wireless fashion. In one embodiment, exercise device 12 may communicate with controller 20 using a local area network or communicate using Internet communication. In embodiments where system 10 includes a single exercise device 12 and wherein controller 20 is incorporated as part of the single exercise device, such communication may be made directly in a wired or wireless fashion, or other transferable means such as USB flash drives.

Figure 2:
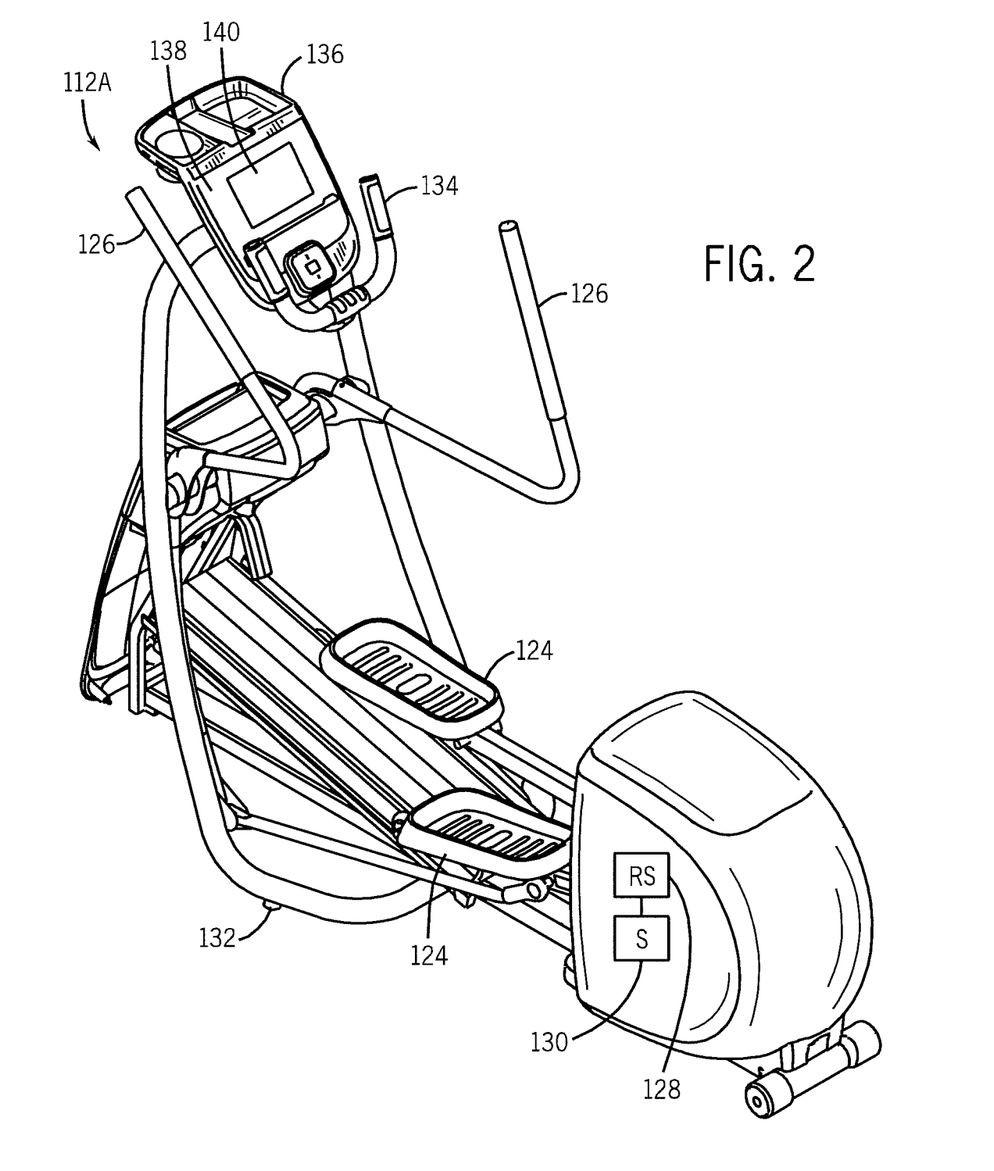
FIG. 2 is a rear perspective view of one example of the next size device of the system of FIG. 1.
Figure 3:
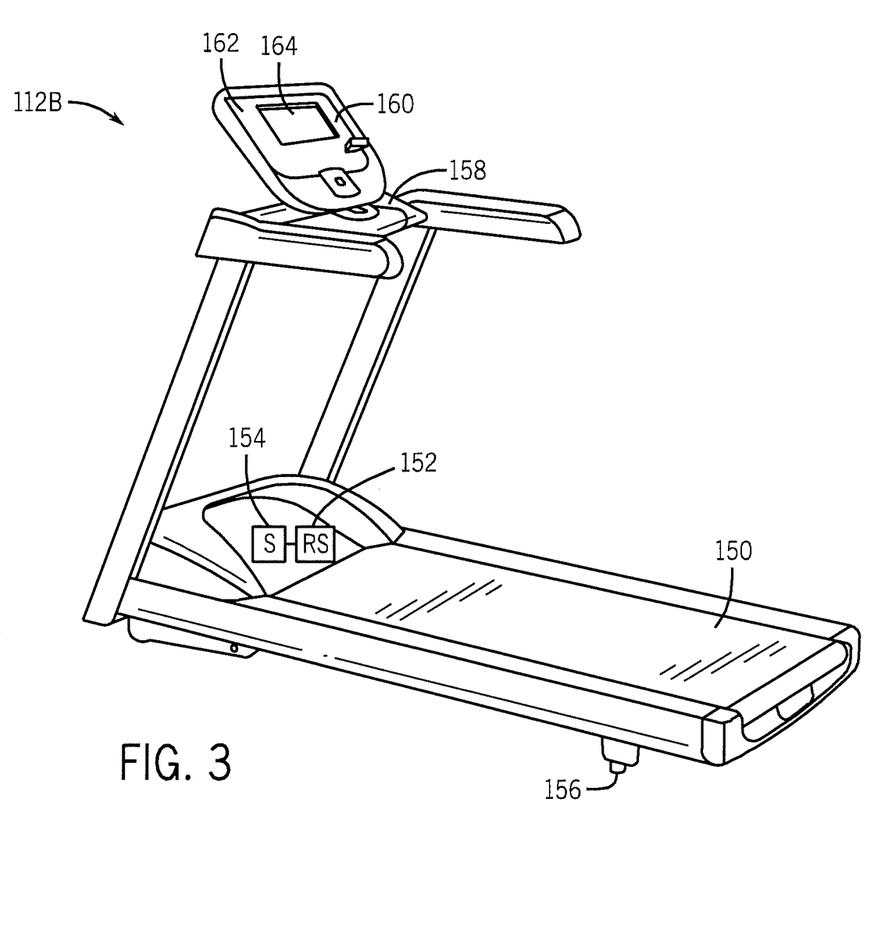
FIG. 3 is a rear perspective view of another embodiment of an exercise device of the system of FIG. 1.

FIGS. 2 and 3 illustrate exercise devices 112A and 112B, specific examples of exercise devices 12A and 12B, respectively. In one embodiment, exercise device 112A comprises an elliptical machine. The elliptical machine 112A generally includes foot supports 124, swing arms 126, one or more resistant sources 128 (schematically shown), one or more sensors 130, body weight sensor 132, body composition sensor 134 and the control panel 136. Foot supports 124 and swing arms 126 are configured to be engaged by an individual who is exercising, wherein the person exercising exerts force or motion against foot supports 124 and swing arms 126 to move such structures against a resistance provided by the one of more resistant sources 128. Resistant sources 130 resist movement of foot supports 124 and swing arms 126. In one embodiment, resistance sources 128 may comprise frictional resistance mechanisms, air brakes, Eddy current brakes, electrical generators or other devices configured to provide a controllable and adjustable resistance to such motion. In one embodiment, resistance sources 128 resist movement of foot supports 124, wherein movement of swing arms 126 is not resisted or wherein swing arms 126 are omitted. The amount or extent of resistance provided by the one of more resistant sources 128 is communicated to controller 20 (shown in FIG. 1).

Sensors 130 comprise one or more sensing devices configured to sense or detect exercise metrics or values such as the speed or rate at which foot supports 124 and potentially swing arms 126 are driven by an individual during a workout. Such sensed values are communicated to controller 20 (shown in FIG. 1). Although resistance sources 128 and sensors 130 are schematically illustrated as being located at a rear of the elliptical exercise device 112A, in other embodiments, resistance sources 128 and sensors 130 may be located at a front of exercise device 112A or at other locations.

Body weight sensor 132 comprises one or more devices configured to detect the weight of an individual. In the example illustrated, sensor 132 comprises pads or feet which sense the weight of an individual. The weight of the individual is determined by sensing the overall weight when a person has mounted exercise device 112A and subtracting the weight of exercise device 112A by itself. The detected body weight of an individual is communicated to controller 20 (shown in FIG. 1).

Sensors 134 comprise devices configured to sense a person's heart rate as well as the percent of body weight that is attributable to lean muscle mass and body fat. In the example illustrated, sensors 134 comprise handgrips configured to detect individual's heart rate as well as his or her body composition based upon an electrical resistance or in other known manners. The detected heart rate and body composition are communicated to controller 20 (shown in FIG. 1). In other embodiments, weight sensor 132 and/or heart rate-body composition sensor 134 may be omitted. For example, in other embodiments, an individual's heart rate may be detected using a chest strap or other similar sensing device. In such embodiments, the weight of an individual or his or her body composition may be entered using input 16 (shown in FIG. 1) or by a connected device such as a wireless scale.

Control panel 136 comprises that part of exercise device 112A by which an individual exercising may interact with exercise device 112A. In particular, control panel 136 facilitates the entry of commands or input of data to exercise device 112A while also providing feedback output to be person or individual exercising. Control panel 136 includes various inputs 138 and one or more displays 140. In one embodiment, one or both of inputs 138 and displays 140 may serve as the input 16 and the display 18 of FIG. 1. In other embodiments, input 16 and display 18 may be provided by other structures separate from exercise device 112A.

As shown by FIG. 3, exercise device 112B comprises an exercise device of a different type as compared to exercise device 112A. As a result, exercise device 112B provides a different type of workout. By increasing the diversity of workouts, exercise device 112 enhances the ability of a person to meet his or her fitness objectives. In the example illustrated, exercise device 112B comprises a treadmill. In other embodiments, exercise devices 112A and 112B may comprise exercise equipment other than an elliptical machine and a treadmill.

Exercise device 112B includes a treadmill belt 150, one or more resistance sources 152 (schematically shown), one of more sensors 154 (schematically shown), body weight sensors 156, heart rate/body composition sensors 158 and a control panel 160. Treadmill belt 150 is configured to be engaged by an individual who is exercising, wherein the person exercising exerts force or motion against belt 150 to move the belt 150 against a resistance provided by the one of more resistant sources 152 or is required to keep pace with the treadmill belt.

Resistance source 152 resists movement of belt 150. In one embodiment, resistance sources 152 may comprise a frictional resistance mechanism, an air brakes, an Eddy current brake, an electrical generator or other devices configured to provide a controllable and adjustable resistance to such motion. The amount or extent of resistance provided by the one of more resistance sources 152 is communicated to controller 20 (shown in FIG. 1).

Sensors 154 comprise one or more sensing devices configured to sense or detect exercise metrics or values such as the speed or rate at which belt 150 is driven by an individual during a workout. Such sensed values are communicated to controller 20 (shown in FIG. 1). Although resistance sources 152 and sensors 154 are schematically illustrated as being located at a front of the treadmill exercise device 112AB, in other embodiments, resistance sources 152 and sensors 154 may be located at a rear of exercise device 112B or at other locations.

Body weight sensor 156 comprises one or more devices configured to detect the weight or mass of an individual. In the example illustrated, sensor 156 comprises pads or feet which sense the weight of an individual. The weight of the individual is determined by sensing the overall weight when a person has mounted exercise device 112B and subtracting the weight of exercise device 112B by itself. The detected body weight of an individual is communicated to controller 20 (shown in FIG. 1). In another embodiment, the weight measuring device is a standalone but is connected to the exercise device wirelessly or in a wired manner.

Sensors 158 comprise devices configured to sense a person's heart rate as well as the percent of body weight that is attributable to lean muscle mass. In the example illustrated, sensors 158 comprise handgrips configured to detect individual's heart rate as well as his or her body composition based upon an electrical resistance or in other known manners. The detected heart rate and body composition are communicated to controller 20 (shown in FIG. 1). In other embodiments, weight sensor 156 and/or sensor 158 may be omitted. In such embodiments, the weight of an individual or his or her body composition may be entered and provided to controller 20 using input 16 (shown in FIG. 1). The person's heart rate may be sensed using other devices.

Control panel 160 comprises that part of exercise device 112B by which an individual exercising may interact with exercise device 112B. In particular, control panel 160 facilitates the entry of commands or input of data to exercise device 112B also providing feedback output to the person or individual exercising. Control panel 160 includes various inputs 162 and one or more displays 164. In one embodiment, one or both of inputs 162 and displays 164 may serve as the input 16 and the display 18 of FIG. 1. In other embodiments, input 16 and display 18 may be provided by other structures separate from exercise device 112B.

As shown by FIG. 1, input 16 comprises one or more devices by which data or information may be provided to controller 20. Input 16 enables an individual to enter his or her fitness objectives as well as other attributes such as his or her age, weight, gender, time available for workouts, frequency per week preferences, available times or days for working out or types of exercise machines to be used for achieving his or her fitness objectives. Input 16 further enables an individual to input requests or commands to controller 20. In one embodiment, input 16 comprises a keyboard, mouse, touchpad, touch screen or other input device. Input 16 may be provided as part of a control panel associated with one of exercise devices 12 or may be a separate input device such as an input device associated with another computer, personal data assistant (PDA) or the like that is in communication with controller 20.

Display 18 comprises one or more devices by which information or data may be output or presented to an individual. Display 18 enables controller 20 to provide information such as an exercise route, exercise parameters, fitness goal objective forecasts and the like. In one embodiment, display 18 may comprise a display screen. In still other embodiments, display 18 may communicate information in other manners such as through the use of light emitting diodes or audible signals such as sounds of voice communication. In one embodiment, display 18 may be provided as part of one of exercise devices 12. In yet other embodiments, display 18 may comprise a screen provided as part of other devices separate from exercise devices 12 such as a display associated with another computer, personal data assistant (PDA) or the like that is in communication with controller 20.

Controller 20 comprises one or more processing units 22 and associated memory 24 configured to provide a person or individual with guidance, motivation and inspirational messaging toward achieving his or her fitness objectives. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 20 may be embodied as part of one or more application-specific integrated circuits (ASICs). Unless otherwise specifically noted, the controller is not limited to any specific combination of hardware circuitry and software, nor to any particular source for the instructions executed by the processing unit.

In the example illustrated, memory 24, which provides instructions to processor 22, includes one or more computer readable programs 26. Computer readable programs 26 comprise computer readable instructions, such as software code, configured to direct the operation of the one more processors 22. The computer readable program 26 are specifically configured to direct the processor 22 to carry out functions or processes including, but not limited to, (1) receiving a fitness objectives for an individual, (2) identifying and storing an excise route for achieving the fitness objectives of an individual using one or more of the exercise devices 12, (3) receiving exercise metrics from the one of more exercise devices 12, (4) comparing the exercise metrics with the exercise route and expected results and (5) based on the comparison, adjusting the previously formed exercise route. The new adjusted exercise route, which includes prescribed workout parameters for multiple individual workouts, is then presented or otherwise displayed to the individual.

As noted above, the computer readable program 26 instructs the one or more processors 22 to receive a fitness objective for an individual. Examples of fitness objectives include, but are not limited to, weight management, fitness management, event preparation and performance enhancement. With the weight management objective, the goal is to attain or maintain the desired weight. With a fitness management objective, the goal might be to attain or maintain a certain level of fitness as measured various physiological markers such as an individual's heart rate given a predefined workout intensity, blood pressure, etc. An event preparation objective might be to prepare for a specific exercise event or competition such as a future race, bicycling event or the like. Finally, a performance enhancement objective might be to achieve or maintain a certain speed or other exercise metric on a particular exercise device or while performing a specific modality or activity.

Once a fitness objective has been received, processor 22, following instructions provided by the computer readable program 26, identifies and stores an exercise route for achieving the fitness objective using one or more of the exercise devices 12. To do so, processor 22 may provide prompts or inquiries via display 18 (as a part of the exercise device or as a separate display) requesting that the individual input certain individual attributes such as his or her age, weight, gender, time available for workouts, frequency per week preferences, preferred exercise devices the date at which the fitness objectives are to be met, and answers to other pertinent questions. Controller 20 may further request information such as the person's weight and body composition. Alternatively, this information may be obtained directly from the exercise device if equipped with such sensors.

Figure 4:
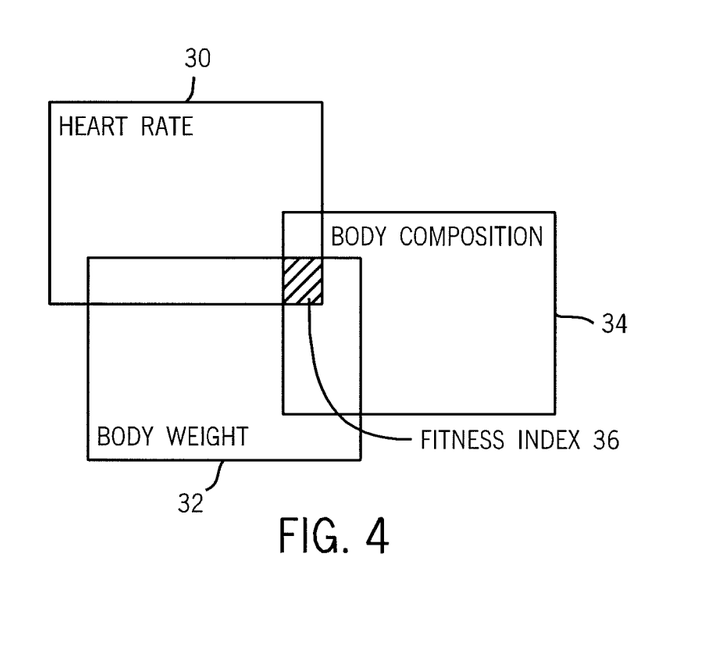
FIG. 4 is a schematic diagram illustrating the identification of a fitness index for use in the creation of an exercise route by the system of FIG. 1.

In addition to requesting the input of such information, controller 20 may also request that the individual complete a fitness evaluation test. In particular, controller 20 may display a fitness test parameter for one of exercise devices 12. Exercise parameters include, but not limited to, a certain speed or rate for a certain duration, a certain level of resistance or a workout intensity. Alternatively, controller 20 may control the exercise device 12 being used for the test such that the noted parameters are set. During exercise by the person as part of the test, controller 20 receives fitness test metrics or the exercise results. In one embodiment, such results are in the form of a heart rate at the prescribed test intensity levels. During the test, exercise device may further detect the individuals body composition and body weight. These values are also communicated to controller 20. At the conclusion of the test workout, controller 20 may ask the individual for his or her assessment of whether the test workout was easy, moderate or hard. As schematically represented by FIG. 4, controller 20 uses each of the test results (heart rate) and sensed attributes (body weight 32 and body composition 34), controller 20 assesses a fitness level or fitness index 36 of the individual and uses the fitness level 36 to identify or create the exercise route.

In particular embodiments, controller 20 may utilize other input or historical information in forming or identifying an exercise route. For example, in one embodiment, controller 20 may additionally include a communication interface 28 by which controller 20 may communicate and receive data or input from external sources. For example, in one embodiment, controller 20 may receive input or historical data from the user, a physician, health care provider, or personal trainer (identified by the individual using input 16) via the communication interface 28. For example, when creating the exercise route, controller 20 may automatically correspond and communicate with a medical record (located at a server of a doctor or health care provider) to gain additional input. In particular embodiments, controller 20 may request authorization the input 16 to gain authorization or access to such data.

Controller 20 stores the identified or generated exercise route and presents the exercise route to the individual via display 18. The generated exercise route may be stored as part of a user profile which may be uploaded to exercise devices 12 by a USB, wireless or wired connection. In particular embodiments, controller 20 may further be configured to automatically transmit or forward the prescribed exercise route as well as exercise objectives to the physician or health care provider.

For purposes of this disclosure, the term "exercise route" means one or more prescribed workout parameters (the parameters of an individual workout) and the frequency (i.e. number of times per week) of each prescribed workout on one or more of exercise devices 12. The exercise route may include individual workout parameters, weekly groupings of workouts and collections of weekly groupings. An exercise route provides an exercise regimen for an individual. An excise route may include multiple distinct types of workouts including, but not limited to, rest (active recovery), active regeneration, lower aerobic, upper aerobic, aerobic power, anaerobic crossover, aerobic power and maximum anaerobic type workouts. In some embodiments, the individual may have the option of selecting or overriding an exercise route. In other embodiments, controller 20 may automatically adjust at least some of the settings of the exercise device to match the exercise parameters or workout parameters of the exercise route based upon where along the route the individual presently resides.

During an individual workout, controller 20 receives exercise metrics or exercise results from a particular exercise device 12. As noted above, such exercise results may include the level of resistance applied by resistance sources 128, 152 (shown in FIGS. 2 and 3) the intensity of the workout, the rate or speed at which the movable members of the exercise device are driven or moved, the duration of the workout or duration of portion or segments of the workout at different intensity levels or different settings, the sensed or detected heart rate of the individual or other metrics or values associated with the workout. During an individual workout, controller 20 may further receive updated results for the individual's body composition and body weight.

Using the received exercise results, controller 20 forms a comparison of the specific exercise results with the expected exercise results based on the recommended exercise route. Based upon this comparison, controller 20, following the instructions of computer readable program 26, adjusts the route. In one embodiment, the adjustment of the route may be further based upon additional input received via communication interface 28 from a physician, health care provider, personal trainer or other information provider.

In one embodiment, such route adjustment may be based upon a degree of compliance to the route. For example, if the individual exercising consistently produces exercise results that are substantially out of compliance and not meeting the prescribed levels of the exercise route, controller 20 may lessen the intensity and lessen the frequency of workouts. The route adjustment may result in a delayed estimated date for attaining the fitness objective. Alternatively, if the individual exercising consistently outperforms the route, controller 20 may increase the intensity, frequency or other parameters of the workouts. In one embodiment, controller 20 is configured to provide the individual with a fitness forecast using the route. Such a fitness forecast tells individual at what time or dates his or her fitness level will achieve certain standards presuming that the route is followed.

Figure 5:
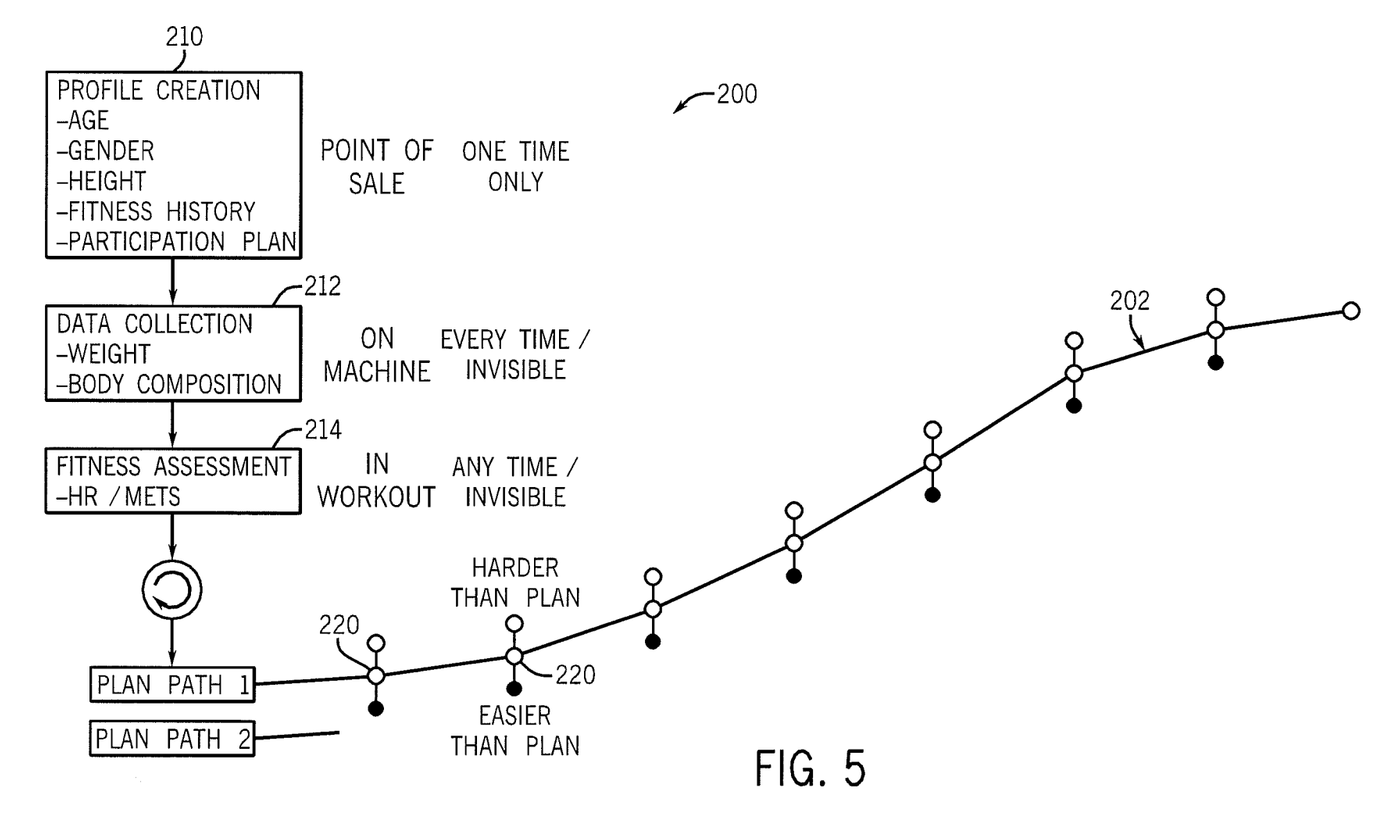
FIG. 5 is a flow diagram of a method used by the system of FIG. 1 to generate the list rated exercise route.

FIG. 5 illustrates one example process 200 by which exercise guidance system 10 creates and adjusts an exercise route 202. As indicated by step 210, system 10 initially may create profile which includes such attributes as an individual's age, gender, height, fitness history and participation plan. Such information may be acquired from the person's physician or health care provider.

As indicated by step 212, system 10 further proceeds with data collection regarding a person's weight and body composition. This data collection may be achieved using input 16 or may be achieved using various sensors on an exercise device. As indicated by step 214, during a workout, system 10 obtained additional fitness assessment information such as a person's heart rate or Mets. Based upon all of the collected data, system 10 generates the illustrated exercise route 202.

Exercise route 202 (also referred to as a "plan path") includes a multitude of individual workouts 220 (illustrated as nodes). After each workout, or after a predefined minimum number of Workouts (to reduce continual adjustment of an exercise route), system 10 adjusts the exercise route. Such adjustment may be such that the excise route is more difficult or alternatively is easier.

The exercise route 202 may be adjusted based upon other factors as well. For example, if controller 20 identifies a trend or pattern of the individual cutting short the duration of each workout, controller 20 may automatically adjust the duration of each workout to better accommodate the individuals' limited time or time demands. In one embodiment, controller 20 may provide the individual with an option of either delaying or prolonging the date for his or her fitness objectives being met or may request to increase the intensity or frequency of the shorter time workouts.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An exercise guidance system comprising:
a first exercise device of a first type;
a display;
a computer readable program configured to:
   receive a fitness objective for an individual;
   identify and store an exercise route for achieving the fitness objective using the first exercise device, the exercise route including recommended workout parameters for a first workout and a second workout subsequent to the first workout;
   receive exercise metrics from the first exercise device during the first workout;
   form a comparison of the exercise metrics with the exercise route to adjust the recommended workout parameters for the second workout of the route based on the comparison; and
   display the adjusted route to the individual on the display.

2. The exercise guidance system of claim 1, wherein the computer readable program is configured to display a goal objective forecast based on the adjusted route, wherein the goal objective forecast comprises a new date at which the fitness objective will be achieved different than a former date at which the fitness objective would have been achieved prior to adjustment of the route.

3. The exercise guidance system of claim 1, wherein the exercise route comprises parameters comprising: workout type, intensity, duration and frequency and wherein the computer readable program is configured to adjust frequency of workouts based upon the comparison, wherein the frequency of workouts comprises a time period between the first workout and the second workout.

4. The exercise guidance system of claim 1, wherein the computer readable program is configured to:
   display a fitness test parameter for the first exercise device;
   receive fitness test metrics of the individual for the first exercise device; and
   assess a fitness level of the individual, wherein the exercise route is based on the fitness level of the individual.

5. The exercise guidance system of claim 1, wherein the computer readable program is configured to adjust the route based on a degree of compliance with workout types, frequency, intensity, and duration parameters of the route.

6. The exercise device of claim 1, wherein the computer readable program is configured to display a fitness evaluation for the individual relative to the goal objective for the individual on the display based on information from the first exercise device including heart rate, body composition and body weight of the individual.

7. The exercise guidance system of claim 1, wherein the route includes individual workout parameters, weekly groupings of workouts and collections of the weekly groupings shown in a day to day workout type and intensity order.

8. The exercise guidance system of claim 1, wherein the route is adjusted to lessen difficulty of parameters when frequency compliance or duration compliance is less than a predetermined value.

9. The exercise guidance system of claim 1, wherein the fitness objective is selected from a group of objectives comprising: weight management, fitness management, event preparation and performance enhancement.

10. The exercise guidance system of claim 1, wherein the computer readable program is configured to receive medical records from a physician and wherein the computer readable program adjusts the route using the medical records.

11. The exercise guidance system of claim 1, wherein the computer readable program is configured to receive input from a health insurer and wherein the computer readable program adjusts the route using the input.

12. The exercise guidance system of claim 1 further comprising:
a second exercise device of a second type different than the first type, wherein the computer readable program is configured to:
receive exercise metrics from the second exercise device;
form a comparison of the exercise metrics from the first exercise device and the second exercise device with the exercise route to adjust recommended workout parameters for the first exercise device during the second workout based on the received exercise metrics from the second exercise device during the first workout forming a part of the comparison; and
display the adjusted route to the individual on the display.

13. The exercise guidance system of claim 12, wherein the first exercise device comprises an elliptical device and wherein the second exercise device comprises a different cardio trainer.

14. A method comprising:
receiving and storing in a persistent storage device a fitness objective for an individual;
identifying and storing an exercise route for achieving the goal objective using one or more exercise devices, the route including prescribed workout parameters for more than one workout;
receiving exercise metrics from a first workout and a second workout subsequent to the first workout;
forming a comparison of the exercise metrics with the exercise route to adjust the recommended workout parameters for the second workout of the route based on the comparison; and
displaying the adjusted route to the individual.

15. The method of claim 14 further comprising displaying a goal objective forecast based on the adjusted route, wherein the goal objective forecast comprises a new date at which the fitness objective will be achieved different than a former date at which the fitness objective would have been achieved prior to adjustment of the route.

16. The method of claim 14 further comprising displaying a degree of compliance to the route, the degree comprising a degree of compliance with respect to a recommended frequency of workouts.

17. An exercise guidance system comprising:
a first exercise device of a first type;
a second exercise device of a second type different than the first type;
a display;
a computer readable program configured to:
receive a fitness objective for an individual;
receiving input from a physician, personal trainer or individual;
identify and store an exercise route for achieving the fitness objective using the first exercise device and the input from one of a physician or a health insurer, the exercise route including prescribed workout parameters for a first workout and a second workout subsequent to the first workout;
receive exercise metrics of the individual from the first exercise device and the second exercise device, the exercise metrics including a determination of workout type, frequency, intensity and duration of workouts;
form a comparison of the exercise metrics with the exercise route to adjust the recommended workout parameters for the second workout of the route based on the comparison; and
display the adjusted route to the individual on the display.

18. The exercise guidance system of claim 1, wherein the computer readable program is further configured to automatically reduce a duration of one or more future workouts in the adjusted route in response to a trend of the individual cutting short a duration of workouts with respect to a recommended duration parameter of the exercise route.

19. The exercise guidance system of claim 18, wherein the computer readable program is further configured to cause the display to present the individual with an option of either delaying a date for attaining the fitness objective or increasing an intensity or frequency of future workouts having a reduced duration.

20. An exercise guidance system comprising:
a first exercise device of a first type;
a display;
a computer readable program configured to:
receive a fitness objective for an individual;
identify and store an exercise route for achieving the fitness objective using the first exercise device, the exercise route including recommended workout parameters for more than one workout;
receive exercise metrics from the first exercise device;
form a comparison of the exercise metrics with the exercise route to adjust the route based on the comparison, wherein the computer readable program is configured to adjust the route based on a degree of compliance with workout types, frequency of workouts, intensity, and duration parameters of the route, wherein the adjustment comprises adjusting recommended workout parameters for a second exercise device of a second type different than the first type; and
display the adjusted route to the individual on the display.

* * * * *